(12) United States Patent
Takahashi et al.

(10) Patent No.: US 8,246,963 B2
(45) Date of Patent: Aug. 21, 2012

(54) **VACCINE FOR *EDWARDSIELLA* DISEASE AND STREPTOCOCCAL DISEASE IN FISH**

(75) Inventors: Yukinori Takahashi, Shimonoseki (JP); Michinari Abe, Saeki (JP)

(73) Assignees: Kyoritsu Seiyaku Corporation, Tokyo (JP); Yukinori Takahashi, Shimonoseki-shi (JP)

( * ) Notice: Subject to any disclaimer, the term of this patent is extended or adjusted under 35 U.S.C. 154(b) by 574 days.

(21) Appl. No.: 12/438,475

(22) PCT Filed: Jun. 5, 2007

(86) PCT No.: PCT/JP2007/000607
§ 371 (c)(1),
(2), (4) Date: Feb. 23, 2009

(87) PCT Pub. No.: WO2008/023453
PCT Pub. Date: Feb. 28, 2008

(65) Prior Publication Data
US 2009/0324648 A1    Dec. 31, 2009

(30) Foreign Application Priority Data
Aug. 24, 2006    (JP) .................................. 2006-228159

(51) Int. Cl.
*A61K 39/02*    (2006.01)
(52) U.S. Cl. .................................. 424/234.1; 424/184.1
(58) Field of Classification Search .......................... None
See application file for complete search history.

(56) References Cited

U.S. PATENT DOCUMENTS

| 2002/0155581 A1 | 10/2002 | Murphy et al. |
| 2004/0146486 A1 | 7/2004 | Sun |

FOREIGN PATENT DOCUMENTS

| JP | 6 503946 | 5/1994 |
| JP | 2003 516148 | 5/2003 |
| JP | 2006 515608 | 6/2006 |

OTHER PUBLICATIONS

Swan et al ; Fish & Shellfish Immunology (2002) ; Abstract only.*
Fisheries Science (1999), 65(4), 527-530.*
Journal of Aquatic Animal Health, (1994) vol. 6, No. 2, pp. 110-117.*
Bulletin of Marine Sciences and Fisheries Kochi University, (Dec. 2000) No. 20, pp. 35-43.*
Matsuyama, Tomomasa et al., "Different sensitivity to *Edwadsiella tarda* in bastard halibut, red sea bream and yellowtail", The Japanese Society of Fish Pathology Taikai Program, p. 50, 2004, (with partial English translation).
Lawrence, Mark L. et al., "Attenuation, Persistence, and Vaccine Potential of an *Edwardsiella ictaluri* purA Mutant", Infection and Immunity, vol. 65, No. 11, pp. 4642-4651, (1997).
Midthun, Karen et al., "Rotavirus Vaccines: an Overview", Clinical Microbiology Reviews, vol. 9, No. 3, pp. 423-434, (1996).
Seki, Makoto et al., "Composition and Usage Standard of M Vac iniae", vol. 42, No. 6, pp. 82-84, 2005, (with partial English translation).
Baeck, Gun Wook et al., "Isolation and characterization of *Streptococcus* sp. from diseased flounder (*Paralichthys olivaceus*) in Jeju Island", Journal of Veterinary Science, vol. 7, No. 1, pp. 53-58, (2006).
Spanish Search Report and Written Opinion Issued Nov. 2, 2011, in Spanish Patent Application No. 200950005.
Andrea Belem COSTA, et al., "Serological Characterization of Atypical Strains of *Edwardsiella tarda* Isolated from Sea Breams", Fish Pathology, vol. 33, No. 4, Oct. 1998, pp. 265-274.
Tomomasa Matsuyama, et al., "Pathogenicity of Motile and Non-motile *Edwardsiella tarda* to Some Marine Fish", Fish Pathology, vol. 40, No. 3, Sep. 2005, pp. 133-135.
Kenji Kawai, et al., "Efficacy of vaccine against Edwarsiellosis of the Japanese flounder, Paralichthys Olivaceus", Bulletin of Marine Sciences and Fisheries Kochi University, AN PREV200100461638, No. 20, Dec. 2000, 1 page (Submitting English Abstract only).
Teruyuki Nakanishi, et al., "Development of a new vaccine delivery method for fish: Percutaneous administration by immersion with application of a multiple puncture instrument", Vaccine, vol. 20, No. 31-32, Nov. 2002, pp. 3764-3769.

* cited by examiner

*Primary Examiner* — Padma Baskar
(74) *Attorney, Agent, or Firm* — Oblon, Spivak, McClelland, Maier & Neustadt, L.L.P.

(57) ABSTRACT

Disclosed is a vaccine for edwardsiellosis and streptococcosis in a fish. Specifically, disclosed is a vaccine for edwardsiellosis in a fish, which comprises inactivated cells of (A) an *Edwardsiella tarda* strain derived from the target fish, and inactivated cells of (B) an *Edwardsiella tarda* strain derived from a fish other than the target fish, wherein, when the strain (A) is a typical *Edwardsiella tarda* strain, the strain (B) is an atypical *Edwardsiella tarda* strain, whereas when the strain (A) is an atypical *Edwardsiella tarda* strain, the strain (B) is a typical *Edwardsiella tarda* strain. Also specifically disclosed is a vaccine for edwardsiellosis and/or streptococcosis in a fish, which comprises the components mentioned above and inactivated cells of (C) *Streptococcus iniae* and/or *Streptococcus parauberis*.

4 Claims, No Drawings

VACCINE FOR *EDWARDSIELLA* DISEASE AND STREPTOCOCCAL DISEASE IN FISH

CROSS-REFERENCE TO RELATED APPLICATIONS

This application is a 371 PCT/JP07/00607 filed Jun. 5, 2007 and claims the benefit of JP 2006-228159 filed Aug. 24, 2006.

TECHNICAL FIELD

The present invention relates to a vaccine for edwardsiellosis or streptococcosis in a fish.

BACKGROUND ART

In recent years, the aquaculture industry has developed remarkably. However, frequent occurrence of viral or bacterial diseases in association with such development has caused great economic losses.

Antibiotics or synthetic antibacterial agents have been used as therapeutic drugs for such bacterial diseases, but satisfactory therapeutic effects have failed to be attained, due to emergence of bacteria resistance to such an antibacterial substance. Moreover, retention of such a therapeutic drug in fish bodies has caused public health problems. Therefore, keen demand has arisen for establishment of measures for fish diseases without use of an antibacterial substance.

In view of the foregoing, development of vaccines is an important issue. Regarding viral diseases, iridoviral disease in, for example, yellowtail, amberjack, and red sea bream has caused great economic losses. However, a commercially available vaccine for such a viral disease has reduced occurrence of the disease. Regarding bacterial diseases, for example, streptococcosis in yellowtail or bastard halibut, and edwardsiellosis in bastard halibut or sea bream, have caused great economic losses. Among these bacterial diseases, the occurrence of streptococcosis in yellowtail has been reduced, by virtue of development of a vaccine therefor.

However, vaccines for bacterial diseases in bastard halibut or sea bream have not yet been satisfactory. Hitherto, attempts have been made to develop a vaccine for edwardsiellosis in bastard halibut, which has caused great economic losses (Non-Patent Document 1). When formalin-killed cells of a bastard halibut-derived *Edwardsiella tarda* strain which is a pathogen are given as a vaccine to a bastard halibut, an antibody to the pathogen is produced in the blood of the bastard halibut, and leukocytes actively phagocytize *E. tarda*. However, the pathogen resists the bactericidal action of leukocytes and survives in leukocytes; i.e., the vaccine does not exhibit the effect of preventing the disease. Thus, a vaccine effective for edwardsiellosis in bastard halibut has not yet been developed so far. For reasons similar to those described above, a vaccine effective for edwardsiellosis in sea bream has not yet been developed.

"Streptococcosis" in bastard halibut collectively refers to diseases caused by *Streptococcus iniae*, *S. parauberis*, and *Lactococcus garvieae*. Although a vaccine for *Streptococcus iniae* infection has been developed, frequent occurrence of *Streptococcus parauberis*-induced disease has caused great economic losses. Therefore, demand has arisen for development of a vaccine for complete prevention of streptococcosis. Meanwhile, in aquaculture farms, edwardsiellosis and streptococcosis co-occur frequently in the form of mixed infection. Therefore, demand has arisen for development of a combination vaccine for exhibiting proper effects on these two diseases.

Non-Patent Document 1: Mekuchi, et al.; Fish Pathology, 30 (4), 251-256: 1995

DISCLOSURE OF THE INVENTION

Problems To Be Solved By the Invention

An object of the present invention is to provide a vaccine effective for edwardsiellosis or streptococcosis in a fish such as bastard halibut or sea bream.

Means for Solving the Problems

The present inventors have found that when inactivated cells of a bastard halibut-derived *Edwardsiella tarda* strain are mixed with inactivated cells of an atypical *Edwardsiella tarda* strain derived from a fish such as red sea bream or crimson sea bream, and the mixture is given as a vaccine to a bastard halibut, in the presence of a mixture of lymphocytes and macrophages isolated from the bastard halibut, the macrophages phagocytize and rapidly kill living cells of a bastard halibut-derived *Edwardsiella tarda* strain. Also, the present inventors have found that when this vaccine is given to a bastard halibut, and the bastard halibut is challenged with *Edwardsiella tarda*, the vaccine exhibits high protective effect against *Edwardsiella tarda*. In addition, the present inventors have found that when this vaccine is employed in combination with whole *Streptococcus iniae* and/or *Streptococcus parauberis*, the resultant combination vaccine is effective for both edwardsiellosis and streptococcosis in bastard halibut. Furthermore, the present inventors have found that when inactivated cells of an *Edwardsiella tarda* strain derived from a target fish other than bastard halibut (e.g., sea bream) are mixed with inactivated cells of a typical or atypical *Edwardsiella tarda* strain derived from the target fish, and the mixture is given as a vaccine to the target fish, the vaccine exhibits high protective effect against *Edwardsiella tarda* in the target fish.

Accordingly, the present invention provides a vaccine for edwardsiellosis in a target fish, comprising inactivated cells of (A) an *Edwardsiella tarda* strain derived from the target fish, and inactivated cells of (B) an *Edwardsiella tarda* strain derived from a fish other than the target fish, wherein, when the strain (A) is a typical *Edwardsiella tarda* strain, the strain (B) is an atypical *Edwardsiella tarda* strain, whereas when the strain (A) is an atypical *Edwardsiella tarda* strain, the strain (B) is a typical *Edwardsiella tarda* strain.

The present invention also provides a vaccine for edwardsiellosis and/or streptococcosis in a target fish, comprising inactivated cells of (A) an *Edwardsiella tarda* strain derived from the target fish; inactivated cells of (B) an *Edwardsiella tarda* strain derived from a fish other than the target fish; and inactivated cells of (C) *Streptococcus iniae* and/or *Streptococcus parauberis*, wherein, when the strain (A) is a typical *Edwardsiella tarda* strain, the strain (B) is an atypical *Edwardsiella tarda* strain, whereas when the strain (A) is an atypical *Edwardsiella tarda* strain, the strain (B) is a typical *Edwardsiella tarda* strain.

Hitherto, occurrence of many infections in cultured fishes has caused great economic losses. However, employment of the vaccine of the present invention can reliably prevent edwardsiellosis in a fish, for which no effective vaccine has yet been developed. Also, employment of the vaccine of the present invention can reliably prevent a mixed infection of *Edwardsiella tarda* and *Streptococcus* in a fish.

BEST MODES FOR CARRYING OUT THE INVENTION

The vaccine for edwardsiellosis in a target fish of the present invention contains inactivated cells of (A) an *Edwardsiella tarda* strain derived from the target fish, and inactivated cells of (B) an *Edwardsiella tarda* strain derived from a fish other than the target fish, wherein, when the strain (A) is a typical *Edwardsiella tarda* strain, the strain (B) is an atypical *Edwardsiella tarda* strain, whereas when the strain (A) is an atypical *Edwardsiella tarda* strain, the strain (B) is a typical *Edwardsiella tarda* strain. As used herein, the term "target fish" refers to a fish to which the vaccine of the present invention is administered.

In the present invention, no particular limitation is imposed on the target fish, so long as it is a fish that is infectable with *Edwardsiella tarda*. Examples of the target fish include fishes for cultivation that are infectable with *Edwardsiella tarda*, such as fishes infectable with typical *Edwardsiella tarda* (e.g., bastard halibut, eel, catfish, and tilapia), and fishes infectable with atypical *Edwardsiella tarda* (e.g., sea bream, crimson sea bream, and yellowtail). Of these, preferred are bastard halibut, eel, catfish, and sea bream, whose infection with *Edwardsiella tarda* may cause great economic losses.

As has been known, typical *Edwardsiella tarda*, which can infect bastard halibut, eel, catfish, or tilapia, is a motile bacterium having peritrichous flagella, whereas atypical *Edwardsiella tarda*, which can infect, for example, red sea bream, crimson sea bream, or yellowtail, is a bacterium that is classified into *Edwardsiella tarda* but differs from typical *Edwardsiella tarda* in that it has neither peritrichous flagella nor motility.

As used herein, "bastard halibut" encompasses fishes for cultivation belonging to the order (or suborder) Pleuronectiformes; specifically, bastard halibut (*Paralichthys olivaceus*), turbot (*Scophthalmus maximus*), barfin flounder (*Verasper moseri*), and spotted halibut (*Verasper variegatus*). As used herein, "sea bream" encompasses fishes for cultivation belonging to the order (or suborder) Perciformes, the family Sparidae; specifically, red sea bream (*Pagus major*), black sea bream (*Acanthopagrus schlegeli*), crimson sea bream (*Evynnis japonica*), and yellow sea bream (*Taius tumifrons*). As used herein, "tilapia" encompasses Nile tilapia (*Oreochromis niloticus*), tilapia mossambica (*Oreochromis mossambicus*), and red tilapia (hybrid of *O. mossambicus* and *O. urolepis hornorum*). As used herein, "yellowtail" encompasses yellowtail (*Seriola quinqueradiata*), amberjack (*Seriola dumerili*), and goldstriped amberjack (*Seriola lalandi*). As used herein, "eel" encompasses Japanese eel (*Anguilla japonica*) and European eel (*Anguilla anguilla*). As used herein, "catfish" encompasses channnel catfish (*Ictalurus punctatus*).

The target-fish-derived *Edwardsiella tarda* strain (A) may be, for example, a strain which is isolated, in an ordinary method, from a target fish infected with *Edwardsiella tarda*. Examples of the bastard halibut-derived *Edwardsiella tarda* strain (A) include OA-3, EH-5, and UH-2. Examples of the red sea bream-derived *Edwardsiella tarda* strain include UT-1, UT-4, and YK-1. Examples of the eel-derived *Edwardsiella tarda* strain include NES-2 and SE-6.

Inactivated cells of such a target-fish-derived *Edwardsiella tarda* strain may be, for example, formalin-killed cells, heat-killed cells, phenol-killed cells, or UV-killed cells. Of these, formalin-killed cells are preferred. Generally, formalin treatment is carried out by adding formalin to a liquid containing cells so as to attain a formalin concentration of 0.3 to 0.7%.

The number of inactivated cells of the target-fish-derived *Edwardsiella tarda* strain (A) is preferably $10^8$ to $10^{11}$ CFU/mL.

As described above, when the *Edwardsiella tarda* strain (A) is a typical *Edwardsiella tarda* strain, the *Edwardsiella tarda* strain (B) (i.e., *Edwardsiella tarda* strain derived from a fish other than the aforementioned target fish) is an atypical *Edwardsiella tarda* strain, whereas when the *Edwardsiella tarda* strain (A) is an atypical *Edwardsiella tarda* strain, the *Edwardsiella tarda* strain (B) is a typical *Edwardsiella tarda* strain. Therefore, for example, when the target fish is bastard halibut, the *Edwardsiella tarda* strain (A) is a typical *Edwardsiella tarda* strain, and thus inactivated cells of the *Edwardsiella tarda* strain (B) are those of an atypical *Edwardsiella tarda* strain (e.g., a sea bream-derived *Edwardsiella tarda* strain). When the target fish is sea bream, the *Edwardsiella tarda* strain (A) is an atypical *Edwardsiella tarda* strain, and thus inactivated cells of the *Edwardsiella tarda* strain (B) are those of a typical *Edwardsiella tarda* strain (e.g., a bastard halibut-derived *Edwardsiella tarda* strain). The *Edwardsiella tarda* strain (B) is isolated, in an ordinary method, from a fish infected with *Edwardsiella tarda*. Inactivation of cells of the *Edwardsiella tarda* strain (B) is carried out in a manner similar to that described above in the case of cells of the target-fish-derived *Edwardsiella tarda* strain.

The number of inactivated cells of the *Edwardsiella tarda* strain (B) is preferably $10^8$ to $10^{11}$ CFU/mL.

The ratio of the number of inactivated cells of the target-fish-derived *Edwardsiella tarda* strain (A) to that of inactivated cells of the *Edwardsiella tarda* strain (B) is preferably 1:(0.1 to 1), particularly preferably 1:(0.5 to 1).

The vaccine for edwardsiellosis and/or streptococcosis in a fish of the present invention contains inactivated cells of the aforementioned *Edwardsiella tarda* strains (A) and (B) and inactivated cells of (C) *Streptococcus iniae* and/or *Streptococcus parauberis*. In this vaccine, preferably, inactivated cells of the *Edwardsiella tarda* strain (A) are those of a bastard halibut-derived *Edwardsiella tarda* strain, and inactivated cells of the *Edwardsiella tarda* strain (B) are those of an atypical *Edwardsiella tarda* strain. That is, this vaccine is preferably a vaccine for edwardsiellosis and/or streptococcosis in bastard halibut.

Inactivated cells of *Streptococcus iniae* may be those of a commonly available strain (e.g., KH-2, ES-1, MK-1, or EY-5). Inactivated cells of *Streptococcus parauberis* may be those of a commonly available strain (e.g., AM-1, AM-4, AK-3, or US-6). Inactivation of cells of such a strain is carried out in a manner similar to that described above in the case of cells of the target-fish-derived *Edwardsiella tarda* strain.

Preferably, inactivated cells of a *Streptococcus iniae* strain are employed in combination with inactivated cells of a *Streptococcus parauberis* strain. The number of inactivated cells of each of these strains is preferably $10^8$ to $10^{11}$ CFU/mL.

Particularly preferably, the vaccine for edwardsiellosis and/or streptococcosis in a fish contains inactivated cells of the following four strains: the target-fish-derived *Edwardsiella tarda* strain (A); the *Edwardsiella tarda* strain (B); a *Streptococcus iniae* strain (C1); and a *Streptococcus parauberis* strain (C2).

The proportions of the numbers of inactivated cells of the strain (A), strain (B), and each of the aforementioned two strains (C) are preferably 1:(0.1 to 1):(1 to 10), particularly preferably 1:(0.5 to 1):(1 to 3). When inactivated cells of the strains (A), (B), (C1), and (C2) are employed in combination as described above, the proportions of the numbers of inactivated cells of the strains (A), (B), (C1), and (C2) are preferably 1:(0.1 to 1):(1 to 10):(1 to 10), particularly preferably 1:(0.5 to 1):(1 to 3):(1 to 3).

The vaccine of the present invention may be provided in the form of a kit including separate drug products, each containing inactivated cells of one of the aforementioned strains. However, the vaccine is preferably provided in the form of a single drug product containing inactivated cells of all the aforementioned strains, from the viewpoint of administration of the vaccine.

The vaccine of the present invention may be provided in the form of injection or oral administration. For the case of injection, saline may be added to the aforementioned inactivated cells. For the case of oral administration, a powdery or granular oral product may be prepared by adding an excipient to the vaccine, or an oral product may be produced by, for example, mixing the vaccine with a feed.

When the vaccine of the present invention is administered to a target fish, for example, the vaccine is injected intramuscularly, intraperitoneally or the like. For the case of injection, preferably, the vaccine (about 0.1 mL) is intramuscularly inoculated into a target fish having a body weight of about 100 g. When the vaccine is inoculated into a target fish having a body weight greatly differing from that described above, the amount of the vaccine inoculated is increased or decreased in accordance with the body weight. For the case of oral administration, preferably, the vaccine (daily dose: 1 to 10 mL/kg body weight) is administered to a target fish for 5 to 10 days by mixing the vaccine with a moist pellet feed, or by spraying, to a solid feed, a suspension prepared by suspending the vaccine in water whose amount is 5 to 10% of the weight of the feed.

The action mechanism of the vaccine of the present invention has not been fully elucidated. However, conceivably, the mechanism of action is attributed not to a specific antigenicity of any of the aforementioned strains (e.g., *Edwardsiella tarda* strain derived from a target fish), but to activation of the bactericidal capacity of phagocytes together with lymphocytes, which capacity is activated only in the case where *Edwardsiella tarda* derived from the target fish is co-present with typical or atypical *Edwardsiella tarda* derived from a fish other than the target fish.

Examples

The present invention will next be described in more detail by way of examples, which should not be construed as limiting the invention thereto.

Example 1

Phagocytic activity of leukocytes from bastard halibut inoculated with the vaccine of the present invention Test method: Bastard halibuts (average body weight: 310 g) were divided into three groups (groups 1 to 3), each including 10 fishes, and the bastard halibuts were reared at a water temperature of 23° C. Bastard halibuts of group 1 (i.e., invention group) were assigned to receive a vaccine produced by mixing equal parts of formalin-killed cells (prepared through formalin treatment following 30-hour culture in Trypto-soya broth at 25° C.) of bastard halibut-derived *Edwardsiella tarda* (*E. tarda*) OA-3 strain (approximate number of cells: $1.8 \times 10^9$ CFU/mL) and formalin-killed cells (prepared in a manner similar to that described above) of red sea bream-derived *E. tarda* UT-1 strain (approximate number of cells: $1.2 \times 10^9$ CFU/mL). Bastard halibuts of group 2 (i.e., control group) were assigned to receive a vaccine produced by using formalin-killed cells (prepared in a manner similar to that described above) of bastard halibut-derived *E. tarda* OA-3 strain (approximate number of cells: $3.6 \times 10^9$ CFU/mL). Bastard halibuts of group 3 (i.e., control group) were assigned to receive Trypto-soya broth containing 0.5% formalin. Each of these vaccines (0.1 mL) was intramuscularly inoculated into a bastard halibut at an upper part of the pectoral fin. Thirty days after vaccine inoculation, blood was collected from five bastard halibuts of each group via the tail blood vessel by use of a syringe treated with heparin sodium. The thus-collected blood was employed in the below-described experiments.

Cells of bastard halibut-derived *E. tarda* OA-3 strain were suspended in saline, and the suspension was allowed to stand still at 60° C. for 10 minutes, followed by centrifugation. Subsequently, the cells were suspended in distilled water so that the number of cells was about $2 \times 10^{10}$ CFU/mL. The cell suspension (2 mL) was added to a plastic petri dish (diameter: 6 cm) and allowed to stand still for one hour. Thereafter, the resultant supernatant was removed by use of a Pasteur pipette, followed by drying with a dryer. Blood (1.5 mL) collected from each of the aforementioned vaccine-inoculated bastard halibuts was added to the petri dish overlaid, and the petri dish was allowed to stand still at 23° C. for 30 minutes. Then, the blood was removed by use of a Pasteur pipette, and the surface of the cells was washed with saline. The petri dish was dried with a dryer, and the cells were fixed with methanol and then subjected to Giemsa Staining. Thereafter, the area of phagocytic plaques was determined under a microscope by use of R1PP2. Table 1 shows test groups employed in Examples 1 and 2.

TABLE 1

Test groups and vaccine types in Examples 1 and 2

| Test group | Vaccine type | Approximate number of cells (CFU/mL) |
|---|---|---|
| Group 1 | Formalin-killed cells of bastard halibut-derived *E. tarda* OA-3 strain | $1.8 \times 10^9$ |
| | Formalin-killed cells of red sea bream-derived *E. tarda* UT-1 strain | $1.2 \times 10^9$ |
| Group 2 (control group) | Formalin-killed cells of bastard halibut-derived *E. tarda* OA-3 strain | $3.6 \times 10^9$ |
| Group 3 (control group) | Trypto-soya broth containing 0.5% formalin | 0 |

Test Results: Table 2 shows the phagocytic activity of leukocytes from bastard halibuts of the invention group and the control groups against cells of the bastard halibut-derived *E. tarda* strain, as determined by the number of plaques in 10 visual fields, the area per one plaque, and the total area of all the plaques. In group 1 or 2, in which bastard halibuts were inoculated with formalin-killed cells of the *E. tarda* strain, the number of plaques (corresponding to the number of leukocytes which phagocytized the bacterial cells) was greater than that in group 3, in which bastard halibuts were inoculated with the culture medium. Particularly in group 1, in which bastard halibuts were inoculated with formalin-killed cells of the bastard halibut-derived and red sea bream-derived *E. tarda* strains, the number of plaques was significantly greater than that in group 2 or 3 ($p<0.05$, 0.01). In group 1, in which bastard halibuts were inoculated with formalin-killed cells of the bastard halibut-derived and red sea bream-derived *E. tarda* strains, the area per one plaque (corresponding to the phagocytic capacity of individual leukocytes) was significantly greater than that of group 2 or 3 ($p<0.05$, 0.01). In group 1 and 2, in this order, the total area of plaques (corresponding to the total phagocytic capacity of leukocytes) was great. Particularly in group 1, the total area of plaques was significantly greater than that in group 2 or 3 (p<0.05, 0.01). These data indicate that when a bastard halibut is inoculated with the vaccine of the present invention (i.e., formalin-killed cells of the bastard halibut-derived and red sea bream-derived *E. tarda* strains), the phagocytic activity of leukocytes against *E. tarda* is significantly enhanced. Meanwhile, even when a bastard halibut was inoculated with formalin-killed cells of the bastard halibut-derived *E. tarda* strain only, leukocytes from the bastard halibut exhibited enhanced phagocytic activity.

TABLE 2

Example 1 Phagocytic activity of leukocytes from bastard halibuts of the invention group and control groups

| Test group | Number of plaques | Area per one plaque ($\mu m^2$) | Total area of plaques ($\mu m^2$) |
|---|---|---|---|
| Group 1 | 318 ± 29*[1] | 233 ± 18*[1] | 74094 ± 10096*[1] |
| Group 2 | 261 ± 27 | 186 ± 20 | 48546 ± 10242 |
| Group 3 | 87 ± 15 | 135 ± 12 | 11745 ± 3069 |

*[1]A significant difference (p < 0.05, 0.01) was observed in phagocytic activity between group 1 and group 2 or 3.

Example 2

Bactericidal Activity of Macrophages From Bastard Halibut Inoculated With the Vaccine of the Present Invention Test method: In a manner similar to that described above, blood was collected from five bastard halibuts (other than the five bastard halibuts from which blood was collected in Example 1) of 10 bastard halibuts of each of the groups shown in Table 1. Macrophages and lymphocytes were separated from the thus-collected blood through Percoll density gradient centrifugation. A sample containing both macrophages (about $1.5 \times 10^5$ cells/mL) and lymphocytes (about $1.5 \times 10^5$ cells/mL) was prepared, and a sample containing only macrophages (about $1.5 \times 10^5$ cells/mL) was also prepared. Each of the samples was suspended in Hanks' solution, and aliquots (0.2 mL each) of the suspension were placed on respective coverslips, followed by culturing at 5% $CO_2$ and 25° C. for one hour. To the resultant culture was added a suspension (0.1 mL) of cells of bastard halibut-derived *E. tarda* OA-3 strain (number of cells: about $3 \times 10^6$ CFU/mL) opsonized with serum derived from the same bastard halibut as that from which leukocytes were derived, and reaction was carried out for one hour under the aforementioned conditions. After completion of reaction, lymphocytes and non-phagocytized bacterial cells were removed from the sample, and the sample on one of the coverslips was subjected to acridine orange staining. Culturing was continued for the samples on the other coverslips, and two hours, three hours, or four hours later, staining was carried out in a manner similar to that described above. Thus, whether or not macrophages killed bacterial cells was observed under a fluorescence microscope.

Test results: Table 3 shows the bactericidal activity of macrophages from bastard halibuts of the invention group and the control groups against cells of the bastard halibut-derived *E. tarda* strain. In Table 3, the bactericidal activity is represented by percent cell killing (%). In group 1 (i.e., invention group), in which bastard halibuts were inoculated with formalin-killed cells of the bastard halibut-derived and red sea bream-derived *E. tarda* strains, the bactericidal activity of macrophages was higher than that in group 2 or 3. Particularly, in the case where reaction was performed for two hours or longer, a significant difference (p<0.05, 0.01) was observed in bactericidal activity between group 1 and group 2 or 3. These data indicated that macrophages from bastard halibuts of group 1 (i.e., invention group) phagocytized bacterial cells and then rapidly killed the bacterial cells. In group 1, when macrophages were co-present with lymphocytes, the bactericidal activity of macrophages was significantly higher (p<0.05) than that in the case where only macrophages were present. This suggests that the effect of lymphocytes on macrophages is enhanced by inoculating bastard halibut with formalin-killed cells of the bastard halibut-derived and red sea bream-derived *E. tarda* strains.

TABLE 3

Example 2 Bactericidal activity of macrophages from bastard halibuts of the invention group and control groups

| Test group | | Reaction time (hr) | | | |
|---|---|---|---|---|---|
| | | 1 | 2 | 3 | 4 |
| Group 1*[1] | Co-presence of macrophages and lymphocytes*[2] | 62 ± 8 | 74 ± 5 | 91 ± 12 | 98 ± 7 |
| | Presence of macrophages only | 43 ± 7 | 58 ± 6 | 64 ± 8 | 76 ± 9 |
| Group 2 | Co-presence of macrophages and lymphocytes | 51 ± 5 | 42 ± 7 | 30 ± 7 | 26 ± 4 |
| | Presence of macrophages only | 40 ± 6 | 38 ± 5 | 29 ± 4 | 22 ± 3 |
| Group 3 | Co-presence of macrophages and lymphocytes | 33 ± 6 | 27 ± 4 | 20 ± 5 | 14 ± 4 |
| | Presence of macrophages only | 36 ± 4 | 29 ± 5 | 18 ± 3 | 15 ± 3 |

*[1]In the case where reaction was performed for two hours or longer, a significant difference (p < 0.05, 0.01) was observed in bactericidal activity between group 1 and group 2 or 3.
*[2]A significant difference (p < 0.05) was observed in bactericidal activity between the case of co-presence of macrophages and lymphocytes and the case of presence of macrophages only.

Example 3

Bactericidal Activity of Macrophages From Bastard Halibut to Which the Vaccine of the Present Invention Has Been Orally Administered Test method: Bastard halibuts (average body weight: 375 g) were divided into two groups (groups 1 and 2), each including five fishes, and the bastard halibuts were reared at a water temperature of 24° C. Bastard halibuts of group 1 (i.e., invention group) were assigned to receive a vaccine produced by mixing equal parts of formalin-killed cells (prepared through formalin treatment following 24-hour culture in Trypto-soya broth at 25° C.) of bastard halibut-derived *E. tarda* OA-3 strain (approximate number of cells: $3.4 \times 10^{10}$ CFU/mL) and formalin-killed cells (prepared in a manner similar to that described above) of red sea bream-derived *E. tarda* UT-1 strain (approximate number of cells: $3.0 \times 10^{10}$ CFU/mL). Bastard halibuts of group 2 (i.e., control group) were assigned to receive a vaccine produced by using formalin-killed cells (prepared in a manner similar to that described above) of bastard halibut-derived *E. tarda* OA-3 strain (approximate number of cells: $6.8 \times 10^{10}$ CFU/mL). Each of these vaccines was mixed with moist pellets so that the daily dose of the vaccine was 1 mL for one bastard halibut, and the mixture was orally administered to each bastard halibut for seven days by use of a syringe having a thin vinyl tube. Thirty days after oral administration, blood was collected from five bastard halibuts of each group via the tail blood vessel by use of a syringe treated with heparin sodium, and the bactericidal activity of macrophages was evaluated in a manner similar to that described in Example 2. Table 4 shows test groups employed in Example 3.

TABLE 4

Test groups and vaccine types in Example 3

| Test group | Vaccine type | Approximate number of cells (CFU/mL) |
|---|---|---|
| Group 1 | Formalin-killed cells of bastard halibut-derived *E. tarda* OA-3 strain | $3.4 \times 10^{10}$ |
|  | Formalin-killed cells of red sea bream-derived *E. tarda* UT-1 strain | $3.0 \times 10^{10}$ |
| Group 2 (control group) | Formalin-killed cells of bastard halibut-derived *E. tarda* OA-3 strain | $6.8 \times 10^{10}$ |

Test results: Table 5 shows the bactericidal activity of macrophages from vaccine-orally administered bastard halibuts of the invention group and the control group against cells of the bastard halibut-derived *E. tarda* strain. In Table 5, the bactericidal activity is represented by percent cell killing (%). In group 1 (i.e., invention group), in which bastard halibuts orally administered a mixture of formalin-killed cells of the bastard halibut-derived *E. tarda* strain and those of the red sea bream-derived *E. tarda* strain, the bactericidal activity of macrophages was higher than that in group 2, in which bastard halibuts orally administered only formalin-killed cells of the bastard halibut-derived *E. tarda* strain. Particularly, in the case where reaction was performed for two hours or longer, a significant difference (p<0.05, 0.01) was observed in bactericidal activity between group 1 and group 2. These data indicated that macrophages from bastard halibuts of group 1 (i.e., invention group) phagocytized bacterial cells and then rapidly killed the bacterial cells. In group 1, when macrophages were co-present with lymphocytes, the bactericidal activity of macrophages was significantly higher (p<0.05) than that in the case where only macrophages were present. This suggests that the effect of lymphocytes on macrophages is enhanced by administering, to bastard halibut, a mixture of formalin-killed cells of the bastard halibut-derived *E. tarda* strain and those of the red sea bream-derived *E. tarda* strain.

TABLE 5

Example 3 Bactericidal activity of macrophages from bastard halibuts of the invention group and control group

|  |  | Reaction time (hr) | | | |
|---|---|---|---|---|---|
|  | Test group | 1 | 2 | 3 | 4 |
| Group 1*[1] | Co-presence of macrophages and lymphocytes*[2] | 57 ± 5 | 69 ± 7 | 80 ± 6 | 86 ± 9 |
|  | Presence of macrophages only | 42 ± 6 | 54 ± 6 | 62 ± 9 | 68 ± 7 |
| Group 2 | Co-presence of macrophages and lymphocytes | 39 ± 7 | 37 ± 4 | 28 ± 4 | 23 ± 3 |
|  | Presence of macrophages only | 41 ± 6 | 30 ± 5 | 21 ± 3 | 18 ± 2 |

*[1] In the case where reaction was performed for two hours or longer, a significant difference (p < 0.05, 0.01) was observed in bactericidal activity between group 1 and group 2.
*[2] A significant difference (p < 0.05) was observed in bactericidal activity between the case of co-presence of macrophages and lymphocytes and the case of presence of macrophages only.

Example 4

Effect of the Vaccine of the Present Invention in Preventing Edwardsiellosis in Bastard Halibut—Study on Appropriate Amount of Antigen Test method: Bastard halibuts (average body weight: 96 g) were divided into eight groups (groups 1 to 8), each including 60 fishes, and bastard halibuts of the eight groups were respectively placed in eight FRP water tanks (2.5 m×1.5 m×1.0 m (height)). The bastard halibuts were reared at a water temperature of 19 to 25° C. for 10 months, during which they were sub-grouped as they grew. Bastard halibuts of groups 1 to 3 (i.e., invention groups) were assigned to receive a vaccine produced by mixing formalin-killed cells (prepared through formalin treatment following 30-hour culture in Trypto-soya broth at 25° C.) of bastard halibut-derived *E. tarda* OA-3 strain and those of red sea bream-derived *E. tarda* UT-1 strain (the number of cells of each strain is shown in Table 6). Bastard halibuts of groups 4 to 6 (i.e., control groups) were assigned to receive a vaccine produced by using formalin-killed cells (prepared in a manner similar to that described above) of bastard halibut-derived *E. tarda* OA-3 strain (the number of cells is shown in Table 6). Bastard halibuts of group 7 (i.e., control group) were assigned to receive a vaccine produced by using formalin-killed cells (prepared in a manner similar to that described above) of red sea bream-derived *E. tarda* UT-1 strain (the number of cells is shown in Table 6). Bastard halibuts of group 8 (i.e., control group) were assigned to receive Trypto-soya broth containing 0.5% formalin.

Each of these vaccines (0.1 mL) was intramuscularly inoculated into a bastard halibut at an upper part of the pectoral fin. One month, six months, or 10 months after vaccine inoculation, 20 bastard halibuts of each group were challenged with cells of *E. tarda* OA-3 strain (which had been cultured in a manner similar to that described above) by immersing the bastard halibuts for 30 minutes in seawater in which *E. tarda* OA-3 cells were suspended (approximate number of cells: $8.5 \times 10^7$ CFU/mL). The thus-challenged bastard halibuts were observed for 30 days after the challenge, and survival rate was determined.

TABLE 6

Test groups and vaccines (number of cells) in Example 4

| Test group | Number of tested fishes | Vaccine type | Number of cells (CFU/mL) |
|---|---|---|---|
| Group 1 | 60 | Formalin-killed cells of bastard halibut-derived E. tarda OA-3 strain | $1.2 \times 10^7$ |
| | | Formalin-killed cells of red sea bream-derived E. tarda UT-1 strain | $1.0 \times 10^7$ |
| Group 2 | 60 | Formalin-killed cells of bastard halibut-derived E. tarda OA-3 strain | $1.2 \times 10^8$ |
| | | Formalin-killed cells of red sea bream-derived E. tarda UT-1 strain | $1.0 \times 10^8$ |
| Group 3 | 60 | Formalin-killed cells of bastard halibut-derived E. tarda OA-3 strain | $1.2 \times 10^{10}$ |
| | | Formalin-killed cells of red sea bream-derived E. tarda UT-1 strain | $1.0 \times 10^{10}$ |
| Group 4 (control group) | 60 | Formalin-killed cells of bastard halibut-derived E. tarda OA-3 strain | $2.4 \times 10^7$ |
| Group 5 (control group) | 60 | Formalin-killed cells of bastard halibut-derived E. tarda OA-3 strain | $2.4 \times 10^8$ |
| Group 6 (control group) | 60 | Formalin-killed cells of bastard halibut-derived E. tarda OA-3 strain | $2.4 \times 10^{10}$ |
| Group 7 (control group) | 60 | Formalin-killed cells of red sea bream-derived E. tarda UT-1 strain | $2.4 \times 10^8$ |
| Group 8 (control group) | 60 | Trypto-soya broth containing 0.5% formalin | 0 |

Test results: Table 7 shows data on survival rate of bastard halibuts of the invention and control groups, as determined following E. tarda challenge performed 1, 6, or 10 months after vaccine inoculation. Among bastard halibuts of the invention groups (groups 1 to 3), which were inoculated with a vaccine produced from formalin-killed cells of the bastard halibut-derived and red sea bream-derived E. tarda strains, the following was revealed. That is, in bastard halibuts of groups 2 and 3, in which the number of cells in the vaccine was $10^8$ to $10^{10}$ CFU/mL, survival rate as determined following E. tarda challenge performed 1, 6, or 10 months after vaccine inoculation was significantly higher (p<0.05, 0.01) than that in bastard halibuts of the control groups (groups 4 to 8). In bastard halibuts of the invention groups, a significant difference (p<0.05) was observed in number of survivals between group 1 and group 2 or 3. These data indicate that when only formalin-killed cells of the bastard halibut-derived or red sea bream-derived E. tarda strain are given, the effect of preventing edwardsiellosis is not sufficiently obtained, whereas when a mixture of formalin-killed cells of the bastard halibut-derived E. tarda strain and those of the red sea bream-derived E. tarda strain is given to a bastard halibut, the effect of protecting the bastard halibut from E. tarda infection is enhanced, and the bastard halibut can be prevented from developing the disease. Also, these data suggest that when the mixture is employed as a vaccine, the appropriate number of formalin-killed cells of the bastard halibut-derived or red sea bream-derived E. tarda strain (i.e., appropriate amount of antigen) is about $10^8$ to about $10^{10}$ CFU/mL.

TABLE 7

Example 4 Survival rate (%) of bastard halibuts of the invention and control groups following E. tarda challenge

| | Month(s) elapsed after vaccine inoculation | | |
|---|---|---|---|
| Test group | 1 | 6 | 10 |
| Group 1 | 75 (15/20)*[1] | 55 (11/20) | 40 (8/20) |
| Group 2*[2,3] | 95 (19/20) | 100 (20/20) | 85 (17/20) |
| Group 3*[2,3] | 90 (18/20) | 95 (19/20) | 90 (18/20) |
| Group 4 (control group) | 30 (6/20) | 35 (7/20) | 15 (3/20) |
| Group 5 (control group) | 50 (10/20) | 45 (9/20) | 30 (6/20) |
| Group 6 (control group) | 55 (11/20) | 40 (8/20) | 30 (6/20) |
| Group 7 (control group) | 45 (9/20) | 35 (7/20) | 25 (5/20) |
| Group 8 (control group) | 15 (3/20) | 25 (5/20) | 20 (4/20) |

*[1](Number of survived fishes/number of tested fishes)
*[2]A significant difference (p < 0.05, 0.01) was observed in survival rate between groups 4 to 8 and groups 2 and 3.
*[3]A significant difference (p < 0.05) was observed in number of survivals (6 months or more after vaccine inoculation) between group 1 and group 2 or 3.

Example 5

Effect of the vaccine of the present invention in preventing edwardsiellosis in bastard halibut—study on mixing ratio of two bacterial strains employed in the vaccine Test method: Bastard halibuts (average body weight: 125 g) were divided into six groups (groups 1 to 6), each including 40 fishes, and bastard halibuts of the six groups were respectively placed in six FRP water tanks (2.5 m×1.5 m×1.0 m (height)). The bastard halibuts were reared at a water temperature of 20 to 25° C. for six months. Bastard halibuts of groups 1 to 4 (i.e., invention groups) were assigned to receive a vaccine produced by mixing formalin-killed cells (prepared through formalin treatment following 30-hour culture in Trypto-soya broth at 25° C.) of bastard halibut-derived E. tarda OA-3 strain and formalin-killed cells (prepared in a manner similar to that described above) of red sea bream-derived E. tarda UT-1 strain (the number of cells of each strain is shown in Table 8). Bastard halibuts of group 5 (i.e., control group) were assigned to receive a vaccine produced by using formalin-killed cells (prepared in a manner similar to that described above) of bastard halibut-derived E. tarda OA-3 strain. Bastard halibuts of group 6 (i.e., control group) were assigned to receive Trypto-soya broth containing 0.5% formalin.

Each of these vaccines (0.1 mL) was intramuscularly inoculated into a bastard halibut at an upper part of the pectoral fin. One month or six months after vaccine inoculation, 20 bastard halibuts of each group were challenged with cells of E. tarda OA-3 strain (which had been cultured in a manner similar to that described above) by immersing the bastard halibuts for 30 minutes in seawater in which E. tarda OA-3 cells were suspended (approximate number of cells: $8.3 \times 10^7$ CFU/mL). The thus-challenged bastard halibuts were observed for 30 days, and survival rate was determined.

TABLE 8

Test groups and vaccines (number of cells) in Example 5

| Test group | Number of tested fishes | Vaccine type | Number of cells (CFU/mL) |
|---|---|---|---|
| Group 1 | 40 | Formalin-killed cells of bastard halibut-derived E. tarda OA-3 strain | $1.4 \times 10^8$ |
|  |  | Formalin-killed cells of red sea bream-derived E. tarda UT-1 strain | $1.2 \times 10^7$ |
| Group 2 | 40 | Formalin-killed cells of bastard halibut-derived E. tarda OA-3 strain | $1.4 \times 10^9$ |
|  |  | Formalin-killed cells of red sea bream-derived E. tarda UT-1 strain | $1.2 \times 10^8$ |
| Group 3 | 40 | Formalin-killed cells of bastard halibut-derived E. tarda OA-3 strain | $1.4 \times 10^9$ |
|  |  | Formalin-killed cells of red sea bream-derived E. tarda UT-1 strain | $1.2 \times 10^9$ |
| Group 4 | 40 | Formalin-killed cells of bastard halibut-derived E. tarda OA-3 strain | $1.4 \times 10^9$ |
|  |  | Formalin-killed cells of red sea bream-derived E. tarda UT-1 strain | $1.2 \times 10^{10}$ |
| Group 5 (control group) | 40 | Formalin-killed cells of bastard halibut-derived E. tarda OA-3 strain | $2.8 \times 10^9$ |
| Group 6 (control group) | 40 | Trypto-soya broth containing 0.5% formalin | 0 |

Test results: Table 9 shows data on survival rate of bastard halibuts of the invention and control groups, as determined following *E. tarda* challenge performed one or six months after vaccine inoculation. Among bastard halibuts of the invention groups (groups 1 to 4), which were inoculated with a vaccine produced from formalin-killed cells of the bastard halibut-derived and red sea bream-derived *E. tarda* strains, the following was revealed. That is, in bastard halibuts of group 2 or 3, in which the number of cells of the bastard halibut-derived *E. tarda* strain was $10^9$ CFU/mL and the number of cells of the red sea bream-derived *E. tarda* strain was $10^8$ CFU/mL or slightly smaller than that of bastard halibut-derived *E. tarda* cells, survival rate as determined following *E. tarda* challenge performed one or six months after vaccine inoculation was significantly higher (p<0.05, 0.01) than that in bastard halibuts of the control groups (groups 5 and 6). In contrast, when the number of formalin-killed cells of the red sea bream-derived *E. tarda* strain was greater by one order than that of formalin-killed cells of the bastard halibut-derived *E. tarda* strain, or was reduced to about $10^7$ CFU/mL, survival rate was low.

These data indicate that the ratio of the number of inactivated cells of the bastard halibut-derived *E. tarda* strain to that of inactivated cells of the red sea bream-derived *E. tarda* strain is important factor for expression of the effects of the vaccine of the present invention.

TABLE 9

Example 5 Survival rate (%) of bastard halibuts of the invention and control groups following E. tarda challenge

|  | Month(s) elapsed after vaccine inoculation | |
|---|---|---|
| Test group | 1 | 6 |
| Group 1 | 65 (13/20)*1 | 55 (11/20) |
| Group 2*2 | 95 (19/20) | 80 (16/20) |
| Group 3*2 | 100 (20/20) | 95 (19/20) |
| Group 4 | 60 (12/20) | 55 (11/20) |
| Group 5 (control group) | 50 (10/20) | 40 (8/20) |
| Group 6 (control group) | 20 (4/20) | 15 (3/20) |

*1(Number of survived fishes/number of tested fishes)
*2A significant difference (p < 0.05, 0.01) was observed in survival rate between the control groups (groups 5 and 6) and groups 2 and 3.

Example 6

Effect of the oral vaccine of the present invention in preventing edwardsiellosis in bastard halibut Test method: Bastard halibuts (average body weight: 108 g) were divided into five groups (groups 1 to 5), each including 60 fishes, and bastard halibuts of the five groups were respectively placed in five FRP water tanks (2.5×1.5×1.0 (height)m). The bastard halibuts were reared at a water temperature of 18 to 26° C. for 10 months. Bastard halibuts of groups 1 to 3 (i.e., invention groups) were assigned to receive a vaccine produced by mixing formalin-killed cells (prepared in a manner similar to that described in Example 4 or 5) of bastard halibut-derived *E. tarda* OA-3 strain and formalin-killed cells (prepared in a manner similar to that described in Example 4 or 5) of red sea bream-derived *E. tarda* UT-1 strain. Bastard halibuts of group 4 (i.e., control group) were assigned to receive a vaccine produced from formalin-killed cells (prepared in a manner similar to that described in Example 4 or 5) of bastard halibut-derived *E. tarda* OA-3 strain. Each of the vaccines was mixed with moist pellets so that the number of cells given to one bastard halibut per day was as shown in Table 10, and the mixture was orally administered to each bastard halibut for seven days by use of a syringe having a thin vinyl tube. A mixture of moist pellets and a culture medium was given to each bastard halibut of group 5 (i.e., control group). One month, six months, or 10 months after oral administration of the vaccine, 20 bastard halibuts of each group were challenged with *E. tarda* cells by immersing the bastard halibuts for 30 minutes in seawater in which *E. tarda* cells were suspended (approximate number of cells: 7.4×10 CFU/mL). The thus-challenged bastard halibuts were observed for 30 days, and survival rate was determined.

TABLE 10

Test groups and vaccines (number of administered cells) in Example 6

| Test group | Number of tested fishes | Vaccine type | Number of cells administered CFU/fish/day |
|---|---|---|---|
| Group 1 | 60 | Formalin-killed cells of bastard halibut-derived E. tarda OA-3 strain | $3.2 \times 10^8$ |
|  |  | Formalin-killed cells of red sea bream-derived E. tarda UT-1 strain | $13.0 \times 10^8$ |
| Group 2 | 60 | Formalin-killed cells of bastard halibut-derived E. tarda OA-3 strain | $3.2 \times 10^9$ |
|  |  | Formalin-killed cells of red sea bream-derived E. tarda UT-1 strain | $3.0 \times 10^9$ |
| Group 3 | 60 | Formalin-killed cells of bastard halibut-derived E. tarda OA-3 strain | $3.2 \times 10^{11}$ |
|  |  | Formalin-killed cells of red sea bream-derived E. tarda UT-1 strain | $3.0 \times 10^{11}$ |
| Group 4 (control group) | 60 | Formalin-killed cells of bastard halibut-derived E. tarda OA-3 strain | $6.4 \times 10^{11}$ |
| Group 5 (control group) | 60 | Trypto-soya broth containing 0.5% formalin | 0 |

Test results: Table 11 shows data on survival rate of bastard halibuts of the invention and control groups, as determined following *E. tarda* challenge performed 1, 6, or 10 months after oral administration of the vaccine. In bastard halibuts of the invention groups (groups 1 to 3), which orally administered a mixture of formalin-killed cells of the bastard halibut-derived *E. tarda* strain and those of the red sea bream-derived *E. tarda* strain, survival rate as determined following *E. tarda* challenge performed 1, 6, or 10 months after vaccine administration was significantly higher (p<0.05, 0.01) than that in bastard halibuts of the control groups (groups 4 and 5). When the dose of the vaccine administered (i.e., the number of cells administered) was greater, survival rate was higher. These data indicate that even when the vaccine of the present invention is orally administered, the vaccine exhibits the effect of preventing edwardsiellosis in bastard halibut.

TABLE 11

Example 6 Survival rate (%) of bastard halibuts of the invention and control groups following *E. tarda* challenge

| Test group | Month(s) elapsed after vaccine inoculation | | |
|---|---|---|---|
|  | 1 | 6 | 10 |
| Group 1*[2] | 75 (15/20)*[1] | 70 (14/20) | 60 (12/20) |
| Group 2*[2] | 85 (17/20) | 75 (15/20) | 65 (13/20) |
| Group 3*[2] | 85 (17/20) | 90 (18/20) | 70 (14/20) |
| Group 4 (control group) | 30 (6/20) | 15 (3/20) | 15 (3/20) |
| Group 5 (control group) | 15 (3/20) | 10 (2/20) | 10 (2/20) |

*[1](Number of survived fishes/number of tested fishes)
*[2]A significant difference (p < 0.05, 0.01) was observed in survival rate between groups 1 to 3 and groups 4 and 5

Example 7

Effect of the Vaccine of the Present Invention in Preventing Edwardsiellosis and Streptococcosis in Bastard Halibut Test method: Bastard halibuts (average body weight: 105 g) were divided into five groups (groups 1 to 5), each including 60 fishes, and bastard halibuts of the five groups were respectively placed in five FRP water tanks (2.5 m×1.5 m×1.0 m (height)). The bastard halibuts were reared at a water temperature of 18 to 25° C. for 10 months, during which they were sub-grouped as they grew. Bastard halibuts of groups 1 to 3 (i.e., invention groups) were assigned to receive a vaccine produced by mixing formalin-killed cells (prepared in a manner similar to that described in Examples 4 to 6) of bastard halibut-derived *E. tarda* OA-3 strain, those (prepared in a manner similar to that described in Examples 4 to 6) of red sea bream-derived *E. tarda* UT-1 strain, formalin-killed cells (prepared through formalin treatment following 20-hour culture in brain heart infusion broth at 25° C.) of bastard halibut-derived *Streptococcus iniae* KH-2 strain, and those (prepared in a manner similar to that described above) of bastard halibut-derived *S. parauberis* AM-1 strain. Bastard halibuts of group 4 (i.e., control group) were assigned to receive a vaccine produced by mixing formalin-killed cells of bastard halibut-derived *E. tarda* OA-3 strain, those of bastard halibut-derived *S. iniae* KH-2 strain, and those of bastard halibut-derived *S. parauberis* AM-1 strain. Table 12 shows the number of formalin-killed cells (used as vaccine) of the aforementioned bacterial strains. No vaccine inoculation was carried out on bastard halibuts of group 5 (i.e., untreated control group).

Each of these vaccines (0.1 mL) was intramuscularly inoculated into a bastard halibut at an upper part of the pectoral fin. One, six, or 10 months after vaccine inoculation, 20 bastard halibuts of each group were intramuscularly inoculated with cultured cells of *S. iniae* KH-2 strain ($6.7 \times 10^4$ CFU/kg body weight) and cultured cells of *S. parauberis* AM-1 strain ($6.7 \times 10^4$ CFU/kg body weight), and, six hours thereafter, the bastard halibuts were challenged with cultured cells of bastard halibut-derived *E. tarda* OA-3 strain by immersing the bastard halibuts for 30 minutes in seawater in which *E. tarda* OA-3 cells were suspended (number of cells: $7.2 \times 10^7$ CFU/mL). The thus-challenged bastard halibuts were observed for 30 days, and survival rate was determined. In addition, bacterial cells were isolated from dead fishes, and pathogen species were identified.

TABLE 12

Test groups and vaccines (number of cells) in Example 7

| Test group | Number of tested fishes | Vaccine type | Number of cells (CFU/mL) |
|---|---|---|---|
| Group 1 | 60 | Formalin-killed cells of bastard halibut-derived *E. tarda* OA-3 strain | $2.5 \times 10^7$ |
| | | Formalin-killed cells of red sea bream-derived *E. tarda* UT-1 strain | $2.3 \times 10^7$ |
| | | Formalin-killed cells of *S. iniae* KH-2 strain | $2.8 \times 10^7$ |
| | | Formalin-killed cells of *S. parauberis* AM-1 strain | $3.1 \times 10^7$ |
| Group 2 | 60 | Formalin-killed cells of bastard halibut-derived *E. tarda* OA-3 strain | $2.5 \times 10^8$ |
| | | Formalin-killed cells of red sea bream-derived *E. tarda* UT-1 strain | $2.3 \times 10^8$ |
| | | Formalin-killed cells of *S. iniae* KH-2 strain | $2.8 \times 10^8$ |
| | | Formalin-killed cells of *S. parauberis* AM-1 strain | $3.1 \times 10^8$ |
| Group 3 | 60 | Formalin-killed cells of bastard halibut-derived *E. tarda* OA-3 strain | $2.5 \times 10^{10}$ |
| | | Formalin-killed cells of red sea bream-derived *E. tarda* UT-1 strain | $2.3 \times 10^{10}$ |
| | | Formalin-killed cells of *S. iniae* KH-2 strain | $2.8 \times 10^{10}$ |
| | | Formalin-killed cells of *S. parauberis* AM-1 strain | $3.1 \times 10^{10}$ |
| Group 4 (control group) | 60 | Formalin-killed cells of bastard halibut-derived *E. tarda* OA-3 strain | $5.0 \times 10^{10}$ |
| | | Formalin-killed cells of *S. iniae* KH-2 strain | $2.8 \times 10^{10}$ |
| | | Formalin-killed cells of *S. parauberis* AM-1 strain | $3.1 \times 10^{10}$ |
| Group 5 (control group) | 60 | Untreated | 0 |

Test results: Table 13 shows data on survival rate of bastard halibuts of the invention and control groups, as determined following bacterial challenge performed 1, 6, or 10 months after vaccine inoculation. In bastard halibuts of the invention groups (groups 1 to 3), which were inoculated with the vaccine (i.e., formalin-killed cells of the bastard halibut-derived and red sea bream-derived *E. tarda* strains, *S. iniae* strain, and *S. parauberis* strain), survival rate as determined following bacterial challenge performed 1, 6, or 10 months after vaccine inoculation was significantly higher (p<0.05, 0.01) than that in bastard halibuts of group 4 (which were inoculated with formalin-killed cells of the bastard halibut-derived *E. tarda* strain, *S. iniae* strain, and *S. parauberis* strain) or bastard halibuts of group 5 (i.e., untreated bastard halibuts). In group 4, in which the number of formalin-killed cells of three bacterial strains (exclusive of the red sea bream-derived *E. tarda* strain) was the same as that in group 3 (invention group), *E. tarda*, *S. iniae*, and *S. parauberis* were isolated from many dead fishes. Meanwhile, a significant difference (p<0.05) was observed in survival rate between bastard halibuts of group 1 (in which the number of formalin-killed cells of the four bacterial strains inoculated as a vaccine was the smallest) and those of group 2 or 3.

These data indicate that the aforementioned vaccine (i.e., mixture of formalin-killed cells of the bastard halibut-derived and red sea bream-derived *E. tarda* strains, *S. iniae* strain, and *S. parauberis* strain) exhibits an excellent effect of preventing edwardsiellosis and streptococcosis in bastard halibut. Meanwhile, a considerable difference was observed in survival rate and isolation frequency of pathogens between bastard halibuts of the invention groups and those of group 4. This indicates that addition of formalin-killed cells of the red sea bream-derived atypical *E. tarda* strain enhances the effect of the vaccine in preventing edwardsiellosis and streptococcosis. The number of inactivated cells of each of the aforementioned strains required for expression of proper effects of the vaccine was determined to be about $10^8$ CFU/mL or more.

TABLE 13

Example 7 Survival rate (%) of bastard halibuts of the invention and control groups following bacterial challenge

| Test group | Month(s) elapsed after vaccine inoculation | | |
|---|---|---|---|
| | 1 | 6 | 10 |
| Group 1*[3] | 65 (13/20)*[1] | 65 (13/20) | 45 (9/20) |
| | Et 5, Si 4, Sp 2*[2] | Et 5, Si 4, Sp 1 | Et 8, Si 6, Sp 3 |
| Group 2*[3,4] | 95 (19/20) | 95 (19/20) | 85 (17/20) |
| | Et 1 | Et 1 | Et 3, Si 2, Sp 1 |
| Group 3*[3,4] | 100 (20/20) | 95 (19/20) | 95 (19/20) |
| | | Et 1 | Et 1, Si 1 |
| Group 4 (control group) | 30 (6/20) | 15 (3/20) | 20 (4/20) |
| | Et 13, Si 8, Sp 6 | Et 15, Si 11, Sp 7 | Et 12, Si 9, Sp 5 |
| Group 5 (control group) | 15 (3/20) | 5 (1/20) | 0 (0/20) |
| | Et 10, Si 16, Sp 11 | Et 17, Si 13, Sp 9 | Et 20, Si 15, Sp 13 |

*[1](Number of survived fishes/number of tested fishes)
*[2]The symbols "Et," "Si," and "Sp" represent *E. tarda*, *S. iniae*, and *S. parauberis*, respectively, and the numeral following each symbol represents the number of dead fishes from which the corresponding bacterium was isolated.
*[3]A significant difference (p < 0.05, 0.01) was observed in survival rate between groups 1 to 3 and groups 4 and 5.
*[4]A significant difference (p < 0.05) was observed in survival rate between group 1 and group 2 or 3.

Example 8

Effect of the Oral Vaccine of the Present Invention in Preventing Edwardsiellosis and Streptococcosis in Bastard Halibut Test method: Bastard halibuts (average body weight: 92 g) were divided into six groups (groups 1 to 6), each including 60 fishes, and bastard halibuts of the six groups were respec tively placed in six FRP water tanks (2.5 m×1.5 m×1.0 m (height)). The bastard halibuts were reared at a water temperature of 19 to 25° C. for 10 months, during which they were sub-grouped as they grew. Bastard halibuts of groups 1 to 4 (i.e., invention groups) were assigned to receive a vaccine produced by mixing formalin-killed cells (prepared in a manner similar to that described in Example 7) of the aforementioned strains (including *S. parauberis* AM-1 strain) (the number of cells of each strain is shown in Table 14). Bastard halibuts of group 5 (i.e., control group) were assigned to receive a vaccine containing no formalin-killed cells of red sea bream-derived *E. tarda* strain. No vaccine inoculation was carried out on bastard halibuts of group 6 (i.e., untreated control group).

Each of these vaccines was suspended in distilled water (amount of water: 10% of the weight of a feed for bastard halibuts) so that the number of formalin-killed cells fed for one bastard halibut per day was as shown in Table 14. The suspension was sprayed to the solid feed and then adsorbed thereon by allowing the thus-sprayed solid feed to stand still for two hours. The resultant solid feed was given to each bastard halibut for 5 or 10 days so that the amount of the feed per day was 2% of the body weight of the fish. One, six, or 10 months after vaccine administration, 20 bastard halibuts of each group were intramuscularly inoculated with cells of *S. iniae* KH-2 strain ($5.6 \times 10^4$ CFU/kg body weight) and cells of *S. parauberis* AM-1 strain ($6.8 \times 10^4$ CFU/kg body weight), and, six hours thereafter, the bastard halibuts were challenged with cultured cells of *E. tarda* OA-3 strain by immersing the bastard halibuts for 30 minutes in seawater in which *E. tarda* OA-3 cells were suspended (number of cells: $8.1 \times 10^7$ CFU/mL). The thus-challenged bastard halibuts were observed for 30 days, and survival rate was determined. In addition, bacterial cells were isolated from dead fishes, and pathogen species were identified.

Test results: Table 15 shows data on survival rate of bastard halibuts of the invention and control groups, as determined following bacterial challenge performed 1, 6, or 10 months after vaccine inoculation. In bastard halibuts of the invention groups (groups 1 to 4), to which a mixture of formalin-killed cells of the bastard halibut-derived and red sea bream-derived *E. tarda* strains, *S. iniae* strain, and *S. parauberis* strain was orally administered as a vaccine for 5 or 10 days, survival rate as determined following bacterial challenge performed 1, 6, or 10 months after vaccine administration was significantly higher (p<0.01) than that in bastard halibuts of the control groups (groups 5 and 6). These data indicate that even when the aforementioned vaccine (i.e., mixture of formalin-killed cells of the bastard halibut-derived and red sea bream-derived *E. tarda* strains, *S. iniae* strain, and *S. parauberis* strain) is orally administered, the vaccine exhibits an excellent effect of preventing edwardsiellosis and streptococcosis in bastard halibut. Meanwhile, a considerable difference was observed in survival rate and isolation frequency of pathogens between bastard halibuts of the invention groups and those of group 5. This indicates that addition, to a vaccine, of formalin-killed cells of the red sea bream-derived atypical *E. tarda* strain enhances the effect of the vaccine in preventing edwardsiellosis and streptococcosis.

TABLE 15

Example 8 Survival rate (%) of bastard halibuts of the invention and control groups following bacterial challenge

| Test group | Month(s) elapsed after vaccine inoculation | | |
|---|---|---|---|
| | 1 | 6 | 10 |
| Group 1*[3] | 65 (13/20)*[1] Et 7, Si 3, Sp 3*[2] | 70 (14/20) Et 5, Si 5, Sp 1 | 55 (11/20) Et 7, Si 6, Sp 5 |

TABLE 14

Test groups and vaccines (number of cells) in Example 8

| Test group | Number of tested fishes | Vaccine type | Number of cells (CFU/mL.fish) | Days of administration |
|---|---|---|---|---|
| Group 1 | 60 | Formalin-killed cells of bastard halibut-derived *E. tarda* OA-3 strain | $5.3 \times 10^8$ | 5 days |
| | | Formalin-killed cells of red sea bream-derived *E. tarda* UT-1 strain | $5.0 \times 10^8$ | |
| | | Formalin-killed cells of *S. iniae* KH-2 strain | $6.1 \times 10^8$ | |
| | | Formalin-killed cells of *S. parauberis* AM-1 strain | $6.7 \times 10^8$ | |
| Group 2 | 60 | Formalin-killed cells of bastard halibut-derived *E. tarda* OA-3 strain | $5.3 \times 10^8$ | 10 days |
| | | Formalin-killed cells of red sea bream-derived *E. tarda* UT-1 strain | $5.0 \times 10^8$ | |
| | | Formalin-killed cells of *S. iniae* KH-2 strain | $6.1 \times 10^8$ | |
| | | Formalin-killed cells of *S. parauberis* AM-1 strain | $6.7 \times 10^8$ | |
| Group 3 | 60 | Formalin-killed cells of bastard halibut-derived *E. tarda* OA-3 strain | $5.3 \times 10^{10}$ | 5 days |
| | | Formalin-killed cells of red sea bream-derived *E. tarda* UT-1 strain | $5.0 \times 10^{10}$ | |
| | | Formalin-killed cells of *S. iniae* KH-2 strain | $6.1 \times 10^{10}$ | |
| | | Formalin-killed cells of *S. parauberis* AM-1 strain | $6.7 \times 10^{10}$ | |
| Group 4 | 60 | Formalin-killed cells of bastard halibut-derived *E. tarda* OA-3 strain | $5.3 \times 10^{10}$ | 10 days |
| | | Formalin-killed cells of red sea bream-derived *E. tarda* UT-1 strain | $5.0 \times 10^{10}$ | |
| | | Formalin-killed cells of *S. iniae* KH-2 strain | $6.1 \times 10^{10}$ | |
| | | Formalin-killed cells of *S. parauberis* AM-1 strain | $6.7 \times 10^{10}$ | |
| Group 5 (control group) | 60 | Formalin-killed cells of bastard halibut-derived *E. tarda* OA-3 strain | $5.3 \times 10^{10}$ | 10 days |
| | | Formalin-killed cells of *S. iniae* KH-2 strain | $6.1 \times 10^{10}$ | |
| | | Formalin-killed cells of *S. parauberis* AM-1 strain | $6.7 \times 10^{10}$ | |
| Group 6 (control group) | 60 | Untreated | 0 | 0 |

TABLE 15-continued

Example 8 Survival rate (%) of bastard halibuts of the invention and control groups following bacterial challenge

| Test group | Month(s) elapsed after vaccine inoculation | | |
|---|---|---|---|
| | 1 | 6 | 10 |
| Group 2*[3] | 75 (15/20) Et 5, Si 3, Sp 1 | 65 (13/20) Et 5, Si 6, Sp 3 | 70 (14/20) Et 6, Si 2, Sp 4 |
| Group 3*[3] | 80 (16/20) Et 4, Si 1, Sp 3 | 70 (14/20) Et 4, Si 5, Sp 2 | 75 (15/20) Et 5, Si 2, Sp 2 |
| Group 4*[3] | 90 (18/20) Et 2, Si 1 | 95 (19/20) Et 1 | 80 (16/20) Et 4, Si 2, Sp 2 |
| Group 5 (control group) | 10 (2/20) Et 18, Si 16, Sp 12 | 25 (5/20) Et 13, Si 12, Sp 11 | 15 (3/20) Et 16, Si 13, Sp 14 |
| Group 6 (control group) | 0 (0/20) Et 20, Si 18, Sp 16 | 10 (2/20) Et 17, Si 15, Sp 14 | 5 (1/20) Et 18, Si 13, Sp 15 |

*[1](Number of survived fishes/number of tested fishes)
*[2]The symbols "Et," "Si," and "Sp" represent *E. tarda*, *S. iniae*, and *S. parauberis*, respectively, and the numeral following each symbol represents the number of dead fishes from which the corresponding bacterium was isolated.
*[3]A significant difference (p < 0.01) was observed in survival rate between groups 1 to 4 (invention groups) and groups 5 and 6 (control groups).

Example 9

Effect of the Vaccine of the Present Invention in Preventing Edwardsiellosis and Streptococcosis in Bastard Halibut—Study on Antigenicity and Preventive Effect of Strains Tested Test method: Bastard halibuts (average body weight: 95 g) were divided into seven groups (groups 1 to 7), each including 60 fishes, and bastard halibuts of the seven groups were respectively placed in seven FRP water tanks (2.5 m×1.5 m×1.0 m (height)). The bastard halibuts were reared at a water temperature of 17 to 26° C. for 10 months, during which they were sub-grouped as they grew. In order to elucidate the relationship between antigenicity and preventive effect of strains tested, bastard halibuts of groups 1 to 3 (i.e., invention groups) and group 5 were assigned to receive a vaccine produced by mixing formalin-killed cells (prepared in a manner similar to that described in Example 7 or 8) of each of bastard halibut-derived *E. tarda* strains of different antigenicity (i.e., OA-3, EH-5, and UH-2), those of each of red sea bream-derived *E. tarda* strains of different antigenicity (i.e., UT-1, UT-4, and YK-1), those of each of *S. iniae* strains of different antigenicity (i.e., KH-2, ES-1, and MK-1), and those of each of *S. parauberis* strains of different antigenicity (i.e., AM-1, AM-4, and AK-3) (the number of formalin-killed cells of each strain is shown in Table 16). Bastard halibuts of group 4 (i.e., control group) were assigned to receive a vaccine containing formalin-killed cells of three strains (exclusive of red sea bream-derived *E. tarda* strain). Bastard halibuts of group 6 were assigned to receive a vaccine containing formalin-killed cells of S. iniae ES-1 strain and *S. parauberis* AM-4 strain. No vaccine inoculation was carried out on bastard halibuts of group 7 (i.e., untreated control group).

Each of these vaccines (0.1 mL) was intramuscularly inoculated into a bastard halibut at an upper part of the pectoral fin. One, six, or 10 months after vaccine inoculation, in a manner similar to that described in Example 7, 20 bastard halibuts of each group were artificially infected (challenged) with bacteria, and the effects of the vaccine were evaluated. Bastard halibuts of group 5 or 6 were artificially infected with *S. iniae* and *S. parauberis*.

TABLE 16

Test groups and vaccines (number of cells) in Example 9

| Test group | Number of tested fishes | Vaccine type | Number of cells (CFU/mL) |
|---|---|---|---|
| Group 1 | 60 | Formalin-killed cells of bastard halibut-derived *E. tarda* OA-3 strain | $2.8 \times 10^9$ |
| | | Formalin-killed cells of red sea bream-derived *E. tarda* UT-1 strain | $2.7 \times 10^9$ |
| | | Formalin-killed cells of *S. iniae* KH-2 strain | $4.5 \times 10^9$ |
| | | Formalin-killed cells of *S. parauberis* AM-1 strain | $3.9 \times 10^9$ |
| Group 2 | 60 | Formalin-killed cells of bastard halibut-derived *E. tarda* EH-5 strain | $3.4 \times 10^9$ |
| | | Formalin-killed cells of red sea bream-derived *E. tarda* UT-4 strain | $3.2 \times 10^9$ |
| | | Formalin-killed cells of *S. iniae* ES-1 strain | $4.4 \times 10^9$ |
| | | Formalin-killed cells of *S. parauberis* AM-4 strain | $3.6 \times 10^9$ |
| Group 3 | 60 | Formalin-killed cells of bastard halibut-derived *E. tarda* UH-2 strain | $3.7 \times 10^9$ |
| | | Formalin-killed cells of red sea bream-derived *E. tarda* YK-1 strain | $3.4 \times 10^9$ |
| | | Formalin-killed cells of *S. iniae* MK-1 strain | $4.7 \times 10^9$ |
| | | Formalin-killed cells of *S. parauberis* AK-3 strain | $4.1 \times 10^9$ |
| Group 4 (control group) | 60 | Formalin-killed cells of bastard halibut-derived *E. tarda* EH-5 strain | $6.8 \times 10^9$ |
| | | Formalin-killed cells of *S. iniae* ES-1 strain | $4.4 \times 10^9$ |
| | | Formalin-killed cells of *S. parauberis* AM-4 strain | $3.6 \times 10^9$ |
| Group 5 (*Streptococcosis* group) | 60 | Formalin-killed cells of bastard halibut-derived *E. tarda* EH-5 strain | $3.4 \times 10^9$ |
| | | Formalin-killed cells of red sea bream-derived *E. tarda* UT-4 strain | $3.2 \times 10^9$ |
| | | Formalin-killed cells of *S. iniae* ES-1 strain | $4.4 \times 10^9$ |
| | | Formalin-killed cells of *S. parauberis* AM-4 strain | $3.6 \times 10^9$ |
| Group 6 (*Streptococcosis* group) | 60 | Formalin-killed cells of *S. iniae* ES-1 strain | $4.4 \times 10^9$ |
| | | Formalin-killed cells of *S. parauberis* AM-4 strain | $3.6 \times 10^9$ |
| Group 7 (control group) | 60 | Untreated | 0 |

Test results: Table 17 shows data on survival rate of bastard halibuts of the invention and control groups, as determined following bacterial challenge performed 1, 6, or 10 months after vaccine inoculation. In bastard halibuts of the invention groups (groups 1 to 3), which were inoculated with a vaccine produced by mixing formalin-killed cells of the different antigenic bastard halibut-derived and red sea bream-derived *E. tarda* strains, *S. iniae* strain, and *S. parauberis* strain, survival rate as determined following bacterial challenge performed 1, 6, or 10 months after vaccine inoculation was significantly higher ($p<0.05$, 0.01) than that in bastard halibuts of group 4, which were inoculated with a vaccine containing no formalin-killed cells of red sea bream-derived *E. tarda* strain, or that in untreated bastard halibuts (control group). In group 4, in which formalin-killed cells of three bacterial strains (exclusive of the red sea bream-derived *E. tarda* strain) were inoculated, and in the untreated control group, *E. tarda*, *S. iniae*, and *S. parauberis* were isolated from dead fishes at high frequency. In bastard halibuts of group 5, which were challenged only with streptococcosis pathogens (*S. iniae* and *S. parauberis*), survival rate was significantly higher than that in bastard halibuts of group 6, which were also challenged only with the streptococcosis pathogens. This indicates that addition of formalin-killed cells of the red sea bream-derived atypical *E. tarda* strain enhances the effect of the vaccine in preventing streptococcosis.

These data show that the effect of the vaccine of the present invention is attributed not to the specific antigenicity of each of the aforementioned four bacterial strains (including bastard halibut-derived *E. tarda* strain), but to the action expressed only when bastard halibut-derived *E. tarda* is co-present with red sea bream-derived *E. tarda*.

TABLE 17

Example 9 Survival rate (%) of bastard halibuts of the invention and control groups following bacterial challenge

| Test group | Month(s) elapsed after vaccine inoculation | | |
|---|---|---|---|
| | 1 | 6 | 10 |
| Group 1[*3] | 95 (19/20)[*1] Et 1[*2] | 85 (17/20) Et 2, Si 1 | 95 (19/20) Et 1 |
| Group 2[*3] | 100 (20/20) | 95 (19/20) Et 1 | 85 (17/20) Et 3, Si 1 |
| Group 3[*3] | 95 (19/20) Et 1 | 95 (19/20) Et 1 | 95 (19/20) Et 1, Si 1 |
| Group 4 (control group) | 40 (8/20) Et 12, Si 8, Sp 11 | 15 (3/20) Et 16, Si 11, Sp 9 | 20 (4/20) Et 16, Si 7, Sp 12 |
| Group 5[*4] Streptococcosis Group | 100 (20/20) | 100 (20/20) | 95 (19/20) Si 1 |
| Group 6 Streptococcosis Group | Si 10, Sp 6 | 45 (9/20) Si 8, Sp 7 | 35 (7/20) Si 7, Sp 4 |
| Group 7 (control group) | 10 (2/20) Et 18, Si 16, Sp 14 | 5 (1/20) Et 18, Si 13, Sp 10 | 0 (0/20) Et 20, Si 15, Sp 13 |

[*1](Number of survived fishes/number of tested fishes)
[*2]The symbols "Et," "Si," and "Sp" represent *E. tarda*, *S. iniae*, and *S. parauberis*, respectively, and the numeral following each symbol represents the number of dead fishes from which the corresponding bacterium was isolated.
[*3]A significant difference ($p < 0.05$, 0.01) was observed in survival rate between groups 1 to 3 and groups 4 and 5.
[*4]A significant difference ($p < 0.05$) was observed in survival rate between group 6 and 5.

Example 10

Effect of the Vaccine of the Present Invention in Preventing Edwardsiellosis in Sea Bream—Study on Appropriate Amount of Antigen Test method: Red sea breams (average body weight: 84 g) were divided into seven groups (groups 1 to 7), each including 60 fishes, and red sea breams of the seven groups were respectively placed in seven FRP water tanks (2.5 m×1.5 m×1.0 m (height)). The red sea breams were reared at a water temperature of 18 to 27° C. for 10 months, during which they were sub-grouped as they grew. For red sea breams of groups 1 to 3 (i.e., invention groups), a vaccine was produced by mixing formalin-killed cells (prepared in a manner similar to that described in Example 4) of bastard halibut-derived *E. tarda* OA-3 strain and those of red sea bream-derived *E. tarda* UT-1 strain (the number of cells of each strain is shown in Table 18). For red sea breams of groups 4 to 6 (i.e., control groups), a vaccine was produced only from formalin-killed cells (prepared in a manner similar to that described above) of red sea bream-derived *E. tarda* UT-1 strain (the number of cells is shown in Table 18). No vaccine inoculation was carried out on red sea breams of group 7 (i.e., untreated control group).

Each of these vaccines (0.1 mL) was intraperitoneally inoculated into a red sea bream. One month, six months, or 10 months after vaccine inoculation, 20 red sea breams of each group were intraperitoneally inoculated (challenged) with cultured cells of red sea bream-derived atypical *E. tarda* UT-1 strain so that the number of cells was $7.3 \times 10^5$ CFU/kg body weight). The thus-inoculated red sea breams were observed for 30 days, and survival rate was determined for evaluation of efficacy of the vaccine.

TABLE 18

| Test group | Number of tested fishes | Vaccine type | Number of cells (CFU/mL) |
|---|---|---|---|
| Group 1 | 60 | Formalin-killed cells of bastard halibut-derived *E. tarda* OA-3 strain | $1.6 \times 10^7$ |
| | | Formalin-killed cells of red sea bream-derived *E. tarda* UT-1 strain | $1.7 \times 10^7$ |
| Group 2 | 60 | Formalin-killed cells of bastard halibut-derived *E. tarda* OA-3 strain | $1.6 \times 10^8$ |
| | | Formalin-killed cells of red sea bream-derived *E. tarda* UT-1 strain | $1.7 \times 10^8$ |
| Group 3 | 60 | Formalin-killed cells of bastard halibut-derived *E. tarda* OA-3 strain | $1.6 \times 10^{10}$ |
| | | Formalin-killed cells of red sea bream-derived *E. tarda* UT-1 strain | $1.7 \times 10^{10}$ |
| Group 4 (control group) | 60 | Formalin-killed cells of red sea bream-derived *E. tarda* UT-1 strain | $3.4 \times 10^7$ |

TABLE 18-continued

| Test group | Number of tested fishes | Vaccine type | Number of cells (CFU/mL) |
|---|---|---|---|
| Group 5 (control group) | 60 | Formalin-killed cells of red sea bream-derived *E. tarda* UT-1 strain | $3.4 \times 10^8$ |
| Group 6 (control group) | 60 | Formalin-killed cells of red sea bream-derived *E. tarda* UT-1 strain | $3.4 \times 10^{10}$ |
| Group 7 (control group) | 60 | Untreated | 0 |

Test results: Table 19 shows data on survival rate of red sea breams of the invention and control groups, as determined following *E. tarda* challenge performed 1, 6, or 10 months after vaccine inoculation. Among red sea breams of the invention groups (groups 1 to 3), which were inoculated with a vaccine produced from formalin-killed cells of the bastard halibut-derived and red sea bream-derived *E. tarda* strains, the following was revealed. That is, in red sea breams of groups 2 and 3, in which the number of formalin-killed cells in the vaccine was $10^8$ to $10^{10}$ CFU/mL, survival rate as determined following E. tarda challenge performed 1, 6, or 10 months after vaccine inoculation was significantly higher (p<0.05, 0.01) than that in red sea breams of groups 4 to 6, which were inoculated only with formalin-killed cells of the red sea bream-derived atypical *E. tarda* strain, or that in untreated red sea breams of group 7. In red sea breams of the invention groups, a significant difference (p<0.05) was observed in survival rate as determined 10 months after vaccine inoculation between red sea breams of group 1 and those of group 2 or 3.

These data indicate that, similar to the case of edwardsiellosis in bastard halibut, in edwardsiellosis in red sea bream, a vaccine containing only formalin-killed cells of the pathogen derived from the corresponding fish does not exhibit proper effects, and that only when formalin-killed cells of the red sea bream-derived atypical *E. tarda* strain are co-present with those of the bastard halibut-derived *E. tarda* strain, an excellent preventive effect is achieved through activation of the bactericidal capacity of phagocytes. Also, these data suggest that when a mixture of formalin-killed cells of the bastard halibut-derived *E. tarda* strain and those of the red sea bream-derived *E. tarda* strain is employed as a vaccine, the appropriate number of formalin-killed cells of each strain (i.e., appropriate amount of antigen) is about $10^8$ to about $10^{10}$ CFU/mL.

TABLE 19

Example 10 Survival rate (%) of red sea breams of the invention and control groups following *E. tarda* challenge

| Test group | Month(s) elapsed after vaccine inoculation | | |
|---|---|---|---|
| | 1 | 6 | 10 |
| Group 1 | 70 (14/20)*[1] | 70 (14/20) | 45 (9/20) |
| Group 2*[2, 3] | 95 (19/20) | 90 (18/20) | 85 (17/20) |
| Group 3*[2, 3] | 100 (20/20) | 100 (20/20) | 90 (18/20) |
| Group 4 (control group) | 40 (8/20) | 30 (6/20) | 35 (7/20) |
| Group 5 (control group) | 40 (8/20) | 40 (8/20) | 30 (6/20) |
| Group 6 (control group) | 50 (10/20) | 45 (9/20) | 45 (9/20) |
| Group 7 (control group) | 15 (3/20) | 20 (4/20) | 5 (1/20) |

*[1](Number of survived fishes/number of tested fishes)
*[2]A significant difference (p < 0.05, 0.01) was observed in survival rate between groups 4 to 7 and groups 2 and 3.
*[3]A significant difference (p < 0.05) was observed in number of survivals (10 months after vaccine inoculation) between group 1 and group 2 or 3.

The invention claimed is:

1. A vaccine for edwardsiellosis in a target fish that is a bastard halibut or a red sea bream, comprising inactivated cells of (A) an *Edwardsiella tarda* strain obtained from the target fish, and inactivated cells of (B) an *Edwardsiella tarda* strain obtained from a fish other than the target fish, wherein, when the strain (A) is a typical *Edwardsiella tarda* strain, the strain (B) is an atypical *Edwardsiella tarda* strain, whereas when the strain (A) is an atypical *Edwardsiella tarda* strain, the strain (B) is a typical *Edwardsiella tarda* strain wherein when the target fish is a bastard halibut, the fish other than the target fish is a red sea bream and when the target fish is a red seam bream, the fish other than the target fish is a bastard halibut.

2. The vaccine according to claim 1, wherein the number of inactivated cells of the strain (A) to that of strain (B) is 1:(0.1 to 1).

3. The vaccine according to claim 1, which is in the form of injection or oral administration.

4. The vaccine according to claim 2, which is in the form of injection or oral administration.

* * * * *